US009459205B1

(12) United States Patent
Margalit

(10) Patent No.: US 9,459,205 B1
(45) Date of Patent: Oct. 4, 2016

(54) REFRACTIVE INDEX MEASUREMENT OF LIQUIDS OVER A BROAD SPECTRAL RANGE

(71) Applicant: EMPIRE TECHNOLOGY DEVELOPMENT LLC, Wilmington, DE (US)

(72) Inventor: Mordehai Margalit, Zichron Yaaqov (IL)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 0 days.

(21) Appl. No.: 14/696,506

(22) Filed: Apr. 27, 2015

(51) Int. Cl.
*G01N 21/41* (2006.01)
*G01J 4/00* (2006.01)

(52) U.S. Cl.
CPC .............. *G01N 21/4133* (2013.01); *G01J 4/00* (2013.01); *G01N 2201/061* (2013.01)

(58) Field of Classification Search
CPC .................... G01N 21/553; G01N 21/554
USPC ................... 356/128–137, 445–448
See application file for complete search history.

(56) References Cited

U.S. PATENT DOCUMENTS

| 4,361,402 | A | * | 11/1982 | Costa | .................. | G01N 21/412 356/128 |
| 2008/0095663 | A1 | * | 4/2008 | Dutta | ..................... | B82Y 20/00 422/400 |
| 2010/0321697 | A1 | * | 12/2010 | Zheng | .................. | G01N 21/553 356/445 |

FOREIGN PATENT DOCUMENTS

EP 00116746 A2 8/1984

OTHER PUBLICATIONS

"Photonic Crystal", Wikipedia, Accessed at <URL: http://web.archive.org/web/20040724060846/http://en.wikipedia.org/wiki/Photonic_crystal> on Sep. 3, 2014, Last modified on Jun. 28, 2004, pp. 2.
"Surface Plasmon", Wikipedia, Accessed at <URL: http://web.archive.org/web/20120304135023/https://en.wikipedia.org/wiki/Surface_plasmon> on Sep. 3, 2014, Last modified on Jan. 26, 2012, pp. 8.
Trevor M . Benson et al., "Micro-Optical Resonators for Microlasers and Integrated Optoelectronics: recent advances and future challenges", Frontiers of Planar Lightwave Circuit Technology: Design, Simulation and Fabrication, 2005, pp. 39-70.
Daniel H. Broaddus et al., "Silicon-Waveguide-Coupled High-Q Chalcogenide Microspheres", Optics Express, Apr. 13, 2009, pp. 5998-6003, vol. 17, No. 8.
S. Buaprathoom et al., "Dual Wavelength Multiple-Angle Light Scattering System for Cryptosporidium Detection", Proceedings of SPIE, 2012, pp. 84272K-1-84272K-12, vol. 8427.

(Continued)

*Primary Examiner* — Hoa Pham
(74) *Attorney, Agent, or Firm* — Ren-Sheng International

(57) ABSTRACT

Techniques described herein generally relate to a refractometer. Using electromagnetic energy, the refractometer can accurately measure refractive index of a liquid without bulky precision optics. By empirically determining a relationship between the refractive index of a liquid sample and a measured reflected power from a resonant structure when in contact with the liquid sample, the refractive index of a liquid can be determined by measuring this reflected power. Furthermore, using multiple light sources of different frequencies, the refractive index of the liquid sample can be determined over a very broad spectral range, for example from ultra-violet to far infrared.

19 Claims, 9 Drawing Sheets

(56) References Cited

OTHER PUBLICATIONS

Dalibor Ciprian et al., "Spectral Interferometry-Based Surface Plasmon Resonance Sensing of Liquid Analyte Refractive Index Change", Proceeding of SPIE, May 3, 2013, vol. 8774.

Dr. Philippe Fauchet et al., "Ultrasensitive Optical Detection of Viruses with Silicon 2-D Photonic Bandgap Structures", Miller Lab, Accessed at <URL: http://web.archive.org/web/20131003173412/http://www.urmc.rochester.edu/labs/Miller-Lab/projects/ultrasensitive_optical_detection_of_viruses_with_silicon_2-d_photonic_bandgap_structures> on Sep. 3, 2014, Last Updated on Oct. 2, 2013, pp. 2.

Hitoshi Suzuki et al., "Refractive Index Measurement of Liquids Using a Dual-color Optical Fiber SPR Sensing System", 5th IEEE Conference on Sensors, Oct. 22-25, 2006, pp. 189-192.

B.H. Tangena et al., "A Novel Approach for Early Warning of Drinking Water Contamination Events", Proceedings of the Water Contamination Emergencies : Monitoring, Understanding and Acting, 2010, pp. 19.

\* cited by examiner

US 9,459,205 B1

REFRACTIVE INDEX MEASUREMENT OF LIQUIDS OVER A BROAD SPECTRAL RANGE

BACKGROUND

Unless otherwise indicated herein, the approaches described in this section are not prior art to the claims in this application and are not admitted to be prior art by inclusion in this section.

Often, trace impurities or other contamination in a material can result in a measurable change in the refractive index value of the material. Consequently, measurement of the refractive index of a material can accurately quantify the presence of such impurities or contamination, particularly in liquids. For example, the refractive index value of liquids or solids can be measured with refractometers, which measure some angle of refraction or the critical angle for total internal reflection of a material. Refractometers are commonly employed for the identification of substances and for quality control of various products, such as wine, sugar, pharmaceuticals, and the like.

SUMMARY

In accordance with at least some embodiments of the present disclosure, an apparatus to determine a refractive index value of a liquid comprises an optical surface, a first electromagnetic emitter, a sensor, and a microprocessor. The optical surface includes a resonant structure configured to be brought into contact with the liquid sample, the first electromagnetic emitter is configured to illuminate the resonant structure using light that has a first optical power in a first wavelength band, and the sensor is configured to receive light reflected from the resonant structure that has a second optical power in the frequency band. The microprocessor is communicably coupled to the electromagnetic emitter and the sensor and is configured to determine a refractive index value of the liquid sample in the frequency band based on the first optical power, the second optical power, and a reference optical power.

In accordance with at least some embodiments of the present disclosure, a method to measure refractive index of a liquid sample that is in contact with an optical surface that includes a resonant structure comprises, while the resonant structure is in contact with the liquid sample, illuminating the resonant structure with light that has a first optical power in a frequency band, measuring light that is reflected off the resonant structure and has a second optical power in the frequency band, and determining a refractive index value of the liquid sample based on the first optical power, the second optical power, and a reference optical power.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
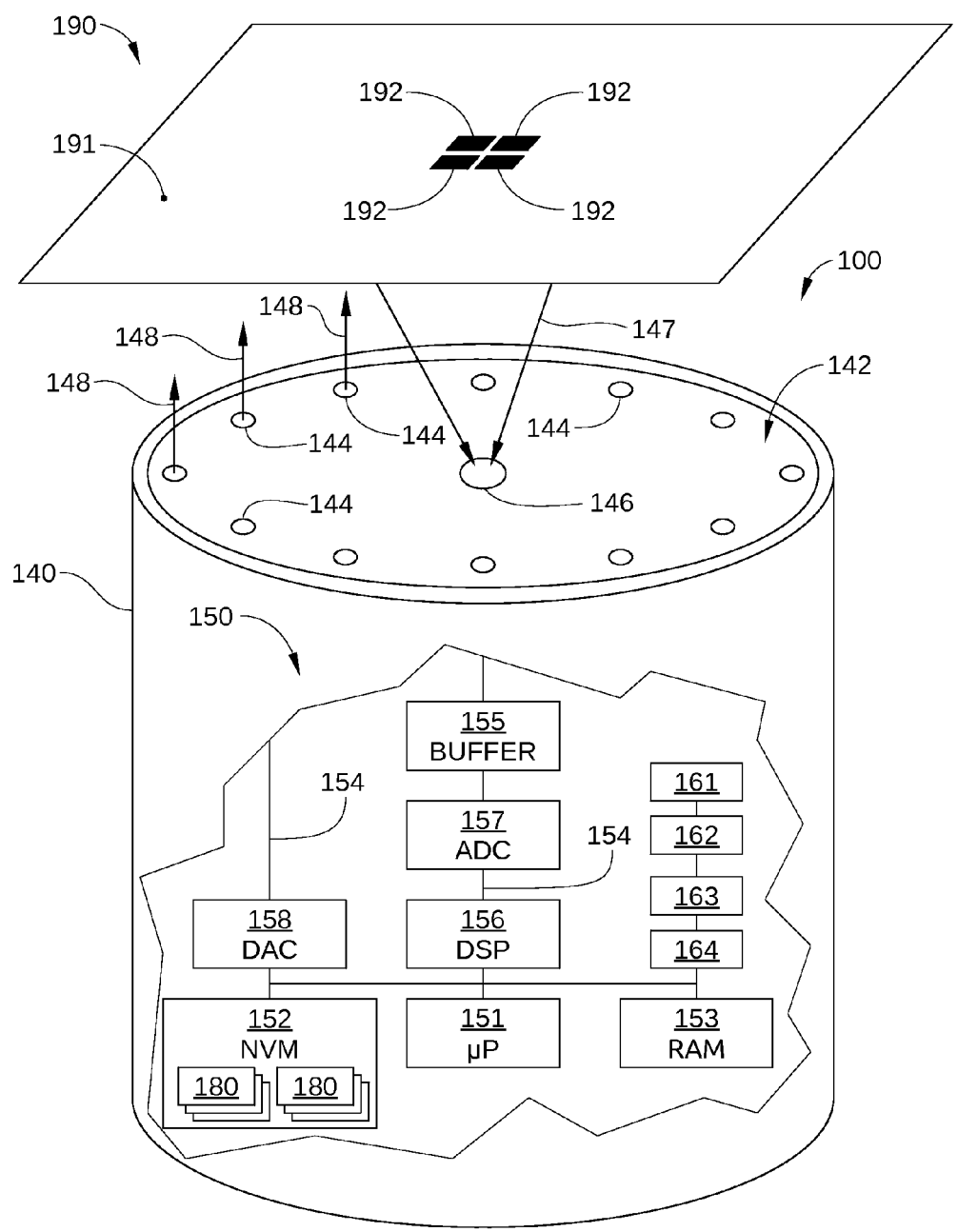
FIG. 1 is an isometric cut-away diagram of a refractometer, arranged in accordance with at least some embodiments of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. The aspects of the disclosure, as generally described herein, and illustrated in the Figures, can be arranged, substituted, combined, and designed in a wide variety of different configurations, all of which are explicitly contemplated and make part of this disclosure.

This disclosure is generally drawn, inter alia, to methods, apparatus, systems, devices, and computer program products related to refractive index measurement of liquids over a broad spectral range.

As noted above, accurate measurement of refractive index value can be used for precise quantification of trace impurities or accurate identification of materials. Refractometers commonly measure refractive index with a prism, and translate changes in the refractive index value into changes in spatial light distribution. Because such devices include precision optical elements and generally require significant free space for accurate spatial measurements, there is a trade-off in such refractometers between precision, cost, and compactness. Accordingly, there is a need in the art for compact, precise, and inexpensive systems and associated methods to measure the refractive index value of a material.

In accordance with at least some embodiments of the present disclosure, apparatus and methods to accurately determine a refractive index value of a liquid are provided. Specifically, electromagnetic energy may be used to quantify refractive index value without the use of precision optics. Furthermore, in some embodiments, the refractive index value of a liquid may be accurately determined over a relatively broad frequency spectrum, rather than for a single frequency of light. This determination of refractive index value for a material over a broad-spectrum may be completed in an automated fashion and without replacing optical components for different frequency bands. One such apparatus is illustrated in FIG. 1.

Figure 2:
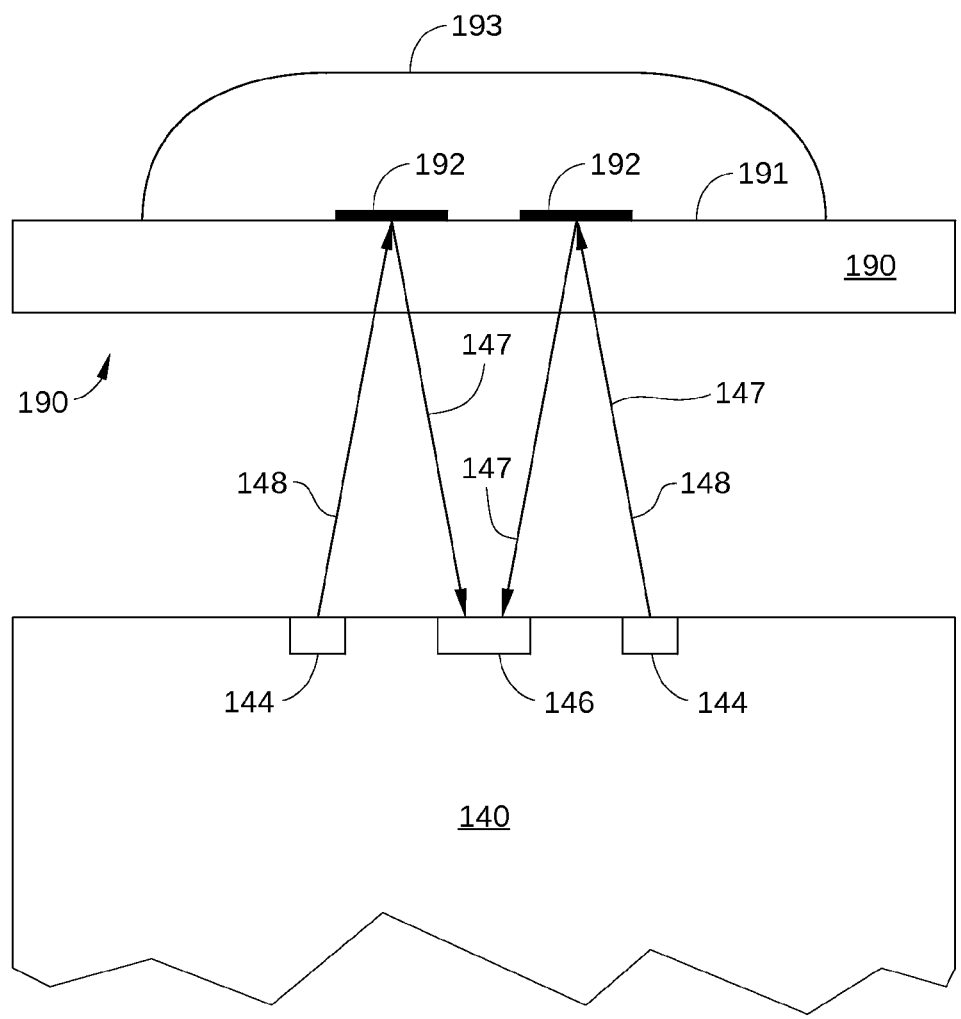
FIG. 2 is a partial schematic side view of the refractometer of FIG. 1, arranged in accordance with at least some embodiments of the present disclosure.

FIG. 1 is an isometric cut-away diagram of a refractometer 100, arranged in accordance with at least some embodiments of the present disclosure. FIG. 2 is a partial schematic side view of refractometer 100, arranged in accordance with at least some embodiments of the present disclosure. Refractometer 100 may include a sample support 190 and a housing 140. In addition, refractometer 100 may further include an opening or window 142 proximate one end of housing 140, one or more sources 144, a sensor array 146, and a control subsystem 150, all contained within housing 140. It is noted that while a plurality of sources 144 are illustrated in FIG. 1, some embodiments of refractometer 100 may employ a single source 144. Moreover, sources 144 may be arranged around the perimeter of window 142 as shown, or in any other technically feasible configuration suitable for illuminating sample support 190.

Sources 144 may be each operable to emit electromagnetic energy 148, and may take a variety of forms. For example, sources 144 may include one or more light emitting diodes (LEDs). Alternatively or additionally, sources 144 may include one or more lasers, for example one or more laser diodes. The lasers may be tunable lasers. Alternatively or additionally, sources 144 may include one or more incandescent sources, such as conventional or halogen light bulbs, or organic LEDs (OLEDs), the latter of which may advantageously be formed on a flexible substrate. One, some, or all of sources 144 may be operable to emit in part or all of an "optical" portion of the electromagnetic spectrum, including the (human) visible portion, the near infrared portion, and/or or the near ultraviolet portion of the electromagnetic spectrum. Additionally or alternatively, sources 144 may be operable to emit electromagnetic energy in other portions of the electromagnetic spectrum, for example the infrared, ultraviolet and/or microwave portions thereof.

In some embodiments, at least some of sources 144 may be operable to emit in or at a different wavelength band than other of sources 144. For example, one or more sources 144 may emit in a wavelength band centered around 450 nm, one or more of sources 144 may emit in a wavelength band centered around 500 nm, and a further source 144 or sources 144 may emit in a band centered around 550 nm. In some embodiments, each source 144 emits in a band centered around a respective frequency or wavelength that is different than the frequency or wavelength associated with each of the other sources 144. Using sources 144 with different band centers advantageously increases the number of frequencies or frequency bands that may be captured from a fixed number of sources 144. This may be particularly advantageous where refractometer 100 is relatively small, and has limited space or footprint for sources 144.

In some embodiments, the distribution of spectral output for each source 144 may vary as a function of drive level (e.g., current, voltage, duty cycle), temperature, and/or other factors, depending on the specific source 144. Such variation may be actively employed to advantageously operate one or more of sources 144 as a plurality of "logical sources," where each of the logical sources is operable to provide different respective emission spectra from a particular source 144. Thus, in such embodiments, the center of the band of emission for each source 144 may vary according to a drive level and/or a temperature of the source 144. For example, the center of the band of emission for LEDs may be varied by adjusting a drive current and/or temperature. One way the spectral content can vary is that the peak wavelength can shift. However, the width of the band, the skew of the distribution, the kurtosis, etc., may also vary. Such variations may be also be advantageously employed to operate sources 144 as a plurality of logical sources. Thus, even if the peak wavelength were to remain constant for a particular source 144, the changes in bandwidth, skew, kurtosis, and any other change in the spectrum may provide useful variations in the output of the source 144 and therefore the operation of refractometer 100. Similarly, the center of the band of emission for sources 144 may be varied when configured as tunable lasers. Varying the center of emission bands for one or more sources 144 advantageously increases the number of different samples that may be captured from a fixed number of sources 144.

Sensor array 146 may include multiple or a single sensing device configured and positioned to receive reflected electromagnetic energy 147 returned from sample support 190. In some embodiments, sensor array 146 may include one or multiple broadband sensors sensitive or responsive over a broad band of wavelengths of electromagnetic energy. Alternatively or additionally, sensor array 146 may include one or multiple narrowband sensors sensitive or responsive over a narrow band of wavelengths of electromagnetic energy. Thus, in some embodiments, sensor array 146 may take the form of several sensor elements, one sensor element being sensitive or responsive to one narrow band of wavelengths, and each of the other sensor elements of sensor array 146 being sensitive or responsive to a different respective narrow band of wavelengths. This approach may advantageously increase the number of samples that may be acquired using a fixed number of sources. In such embodiments the narrow bands may or may not overlap. For example, in some embodiments, sensor array 146 may include four photosensors: two for measuring light in the visible spectrum, one for infrared, and one for ultraviolet.

Sensor array 146 may take a variety of forms suitable for sensing or responding to electromagnetic energy. For example, sensor array 146 may include one or more photodiodes (e.g., germanium photodiodes, silicon photodiodes), photomultiplier tubes, CMOS image sensors, charge coupled devices (CCDs), and/or micro-channel plates. Furthermore, any other forms of electromagnetic sensors may be employed suitable to detect the wavelengths expected to be returned in response to the particular illumination and properties of sample support 190 when illuminated by sources 144.

Control subsystem 150 may include a microprocessor 151 and computer-readable media, for example one or more memories such as a nonvolatile memory (NVM) 152, e.g., flash memory or read only memory (ROM), and a random access memory (RAM) 153. One or more buses 154 in control subsystem 150 may couple nonvolatile memory 152 and RAM 153 to microprocessor 151. Buses 154 may take a variety of forms including an instruction bus, data bus, other communications bus and/or power bus. Nonvolatile memory 152 may store instructions and/or data (e.g., reference intensities 180) for controlling refractometer 100. Volatile RAM 153 may store instructions and/or data for use during operation of refractometer 100.

Control subsystem 150 may optionally include a buffer 155 to buffer information received from sensor array 146. Control subsystem 150 may further include a digital signal processor (DSP) 156 coupled to buses 154 and configured to process information received from sensor array 146 via buffer 155. Control subsystem 150 may further include an analog-to-digital converter (ADC) 157 and/or a digital-to-analog converter (DAC) 158. ADC 157 may, for example, be used for converting analog photodiode responses into digital data for further analysis and/or transmission. DAC 158 may, for example, be used for converting digital computer commands into analog LED current levels. Control subsystem 150 may additionally or alternatively include an analog signal processor, which may be particularly useful where sensor array 146 includes one or more photodiodes.

In addition, control subsystem 150 may include a user interface including one or more user interface devices. For example, control subsystem 150 may include one or more speakers or microphones 161 and/or visual indicators 162, such as one or more LEDs, liquid crystal displays (LCD), or other visual indicators. The LCDs may, for example, include a touch-sensitive LCD configured to display a graphical user interface that is operable by a user of refractometer 100. Additionally or alternatively, control subsystem 150 may include one or more user-operable input elements 163, such as switches or keys turning the test device ON and OFF and/or for controlling the operation of refractometer 100, for example, downloading or uploading data or instructions to or from refractometer 100. Control subsystem 150 may further include one more communication ports 164, for example, a USB port, an infrared transceiver, or an RF transceiver, that allow the transmission of data, instructions, and/or results, to or from refractometer 100.

Microprocessor 151 may be configured to employ instructions and/or data from nonvolatile memory 152 and RAM 253 in controlling operation of refractometer 100. For example, microprocessor 151 may operate sources 144 in one or more illumination sequences. The illumination sequences determine an order in which sources 144 are turned on and off, and indicate an ordered pattern of drive levels (e.g., current levels, voltage levels, duty cycles) for sources 144. Thus, for example, microprocessor 151 may cause the application of different drive levels to different respective sources 144 to cause each of the respective sources 144 to emit electromagnetic energy in multiple distinct bands of the electromagnetic spectrum. DSP 156 and/or microprocessor 151 may then process information generated by sensor array 146, the information being indicative of the response of sample support 190 to illumination by each of sources 144 or a combination of sources 144. It is noted that refractometer 100 may be fabricated using bulk commodity components and, because sophisticated optics are not used, is relatively simple to manufacture. Consequently, refractometer 100 may be an inexpensive alternative to current refractometer technology.

Sample support 190 may include a surface 191 configured to support a liquid sample for analysis by refractometer 100. In addition, sample support 190 may include one or more resonant structures 192 formed on surface 191. For example, in some embodiments, sample support 190 may be a glass plate on which a liquid sample may be disposed and through which electromagnetic energy 148 may be transmitted from sources 144 (sources 144 are described below). In the embodiment illustrated in FIG. 1, sample support 190 is configured to support a droplet 193 of a liquid sample disposed on top of and in contact with resonant structures 192. In other embodiments, sample support 190 may be configured to immerse resonant structures 192 in a liquid sample, for example when window 142 is disposed on a bottom surface of housing 140 and sample support 190 is disposed below housing 140. Furthermore, any other configuration of housing 140 and sample support 190 that maintains contact between a liquid sample and resonant structures 192 may be employed in refractometer 100.

In some embodiments, a liquid sample may be considered "in contact" with resonant structures 192 by simply wetting an exposed surface or surfaces of resonant structures 192. In some embodiments, for example when resonant structures 192 include a photonic crystal with a three-dimensional arrangement of particles and/or voids, a liquid sample may be considered to be in contact with resonant structures 192 when a portion of the liquid sample penetrates such voids, since the photonic crystal will have a more pronounced effect. In other embodiments in which resonant structures 192 include a photonic crystal with a three dimensional arrangement of particles and/or voids, the liquid sample may be considered in contact with the resonant structure by wetting but not penetrating such voids, since the optical field confined in the resonant structure has an evanescent component extending outside the structure and into the liquid sample. In such embodiments, the liquid sample may be considered to be in contact with resonant structures 192 if such an evanescent field extends into the liquid sample. Thus, in such embodiments, the liquid sample may be in contact with resonant structures 192 even in the liquid sample does not diffuse into voids included in resonant structures 192. In the embodiment illustrated in FIG. 1, sample support 190 is separated from window 142 of housing 140, either by free space or by one or more optical elements, such as one or more lenses, prisms, polarizers, wave plates, and/or filters. In other embodiments, sample support 190 may be in direct contact with window 142, or may be configured as window 142. Any other technically feasible positioning of sample support 190 with respect to housing that allows sources 144 to illuminate resonant structures 192 may be employed in refractometer 100. In some embodiments, sample support 190 and window 142 may be separated by one or more optical elements configured to linearly polarize electromagnetic energy 148 prior to illuminating resonant structures 192, for example, when one or more of resonant structures 192 are configured to generate surface plasmon resonance when illuminated by suitably polarized light.

Resonant structures 192 may be any optical surface operable to reflect incident light, e.g., electromagnetic energy 148, with a particular frequency or in a particular frequency band. Example structures suitable for use as one or more of resonant structures 192 any structure configured so that the reflected optical power for light having a particular frequency or in a particular frequency band varies as a function of the refractive index value of the liquid sample. For example, in some embodiments, resonant structure 192 may include a photonic crystal with a photonic band gap that overlaps at least a portion of the frequency band of light incident on resonant structure 192. In such embodiments, three-dimensional photonic crystals deposited on a suitable surface may be configured for use in the optical and near-optical wavelength range.

In other embodiments, resonant structure 192 may include a structure configured to generate a surface plasmon that at least partially reflects light with a frequency in the frequency band of incident light (e.g., electromagnetic energy 148). In such embodiments, the light used to illuminate resonant structure 192 may be p-polarized light, since s-polarized light generally cannot generate surface plasmons when incident on resonant structure 192. Moreover, in such embodiments, a thin metal film formed on a glass plate may be configured to generate such a surface plasmon. Metals that may be included in such a structure include silver, gold, copper, titanium, chromium, combinations thereof and alloys thereof. The thickness of such a metal film depends on the index of refraction of the glass plate and the frequency band in which resonant structure 192 is intended to reflect incident light. A suitable thickness of and methods for depositing such a film can be readily determined by one of skill of the art. Other resonant structures that may be used for resonant structure 192 include micro spheres deposited or optical micro cavities formed into an optical surface (e.g., on surface 191).

Each of resonant structures 192 may be selected to have a respective reflected frequency band that reflects at least a portion of incident light with a frequency that is within the reflected frequency band of the resonant structure 192. Alternatively or additionally, the particular frequency or frequency band of electromagnetic energy 148 output by each source 144 may be selected to be at least partially within the reflected frequency band of a corresponding resonant structure 192. In either case, the reflected frequency band of each of resonant structures 192 at least partially overlaps with the frequency or frequency band of electromagnetic energy 148 incident thereon, as illustrated in FIG. 3.

Figure 3:
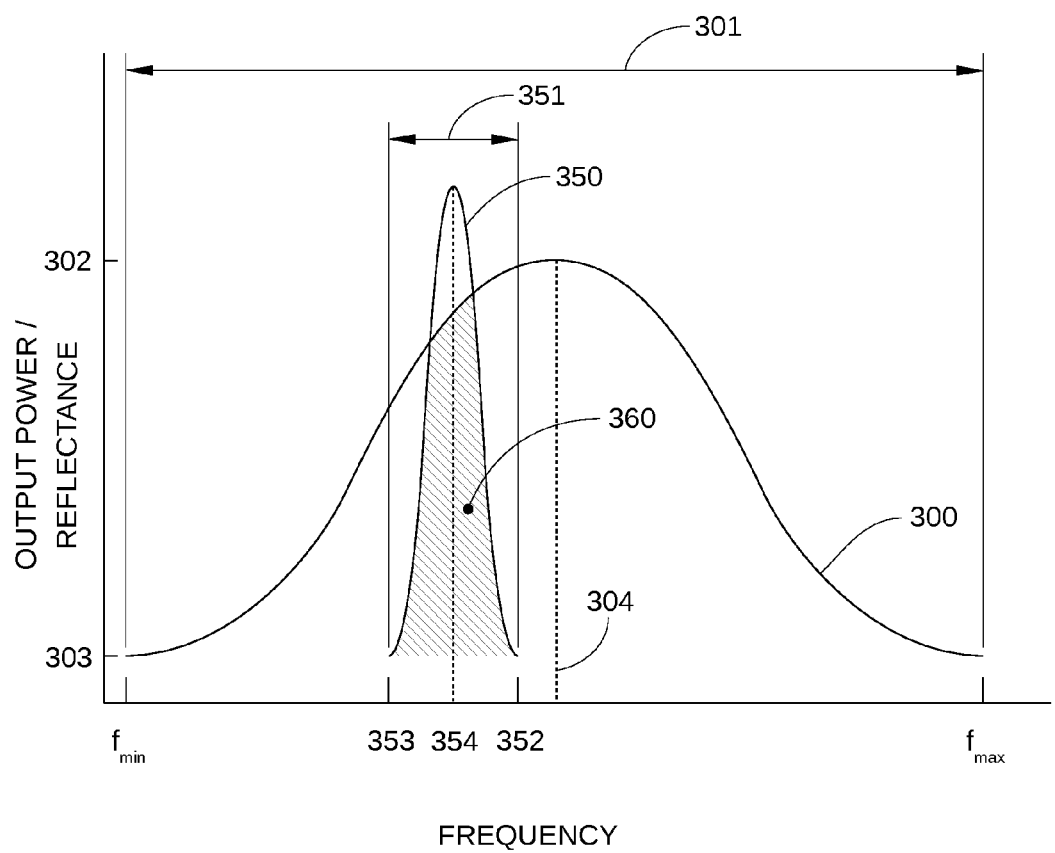
FIG. 3 shows an example reflectance profile for one of the resonant structures in FIG. 1 and an example output spectrum for one of the sources in FIG. 1, in accordance with at least some embodiments of the present disclosure.

FIG. 3 shows an example reflectance profile 300 for one of resonant structures 192 of FIG. 1 and an example output spectrum 350 for one of sources 144 of FIG. 1, in accordance with at least some embodiments of the present disclosure. Reflectance profile 300 illustrates a reflectance (y-axis) with respect to the frequency of incident light (x-axis), such as electromagnetic energy 148 of FIGS. 1 and 2 from one or more of sources 144 of FIGS. 1 and 2. Output spectrum 350 illustrates output power (y-axis) with respect to the frequency of light (x-axis) emitted by source 144. Reflectance profile 300 of a particular resonant structure 192 typically includes a reflected frequency band 301, a maximum reflectance 302, a minimum reflectance 303, and a peak reflectance frequency 304, and output spectrum 350 of an example source 144 includes an output frequency band 351, a maximum output frequency 352, a minimum output frequency 353, and a peak output frequency 354.

Reflected frequency band 301 of reflectance profile 300 indicates a band of light frequencies that are at least partially reflected from a particular resonant structure 192. By contrast, frequencies of light that are incident on the resonant structure 192 but fall outside reflected frequency band 301 are either transmitted or absorbed, and very little or none of such incident light is reflected. Thus, in FIG. 3, reflected frequency band 301 extends from a minimum frequency $f_{min}$ to a maximum frequency $f_{max}$, and light with a frequency less than minimum frequency $f_{min}$ or greater than maximum frequency $f_{max}$ is entirely or almost entirely transmitted and/or absorbed by resonant structure 192.

Maximum reflectance 302 indicates the highest reflectance of the particular resonant structure 192 of the resonant structure associated with reflectance profile 300. Depending on the configuration of resonant structure 192, maximum reflectance 302 may be as high as about 100% of incident light. Minimum reflectance 303 indicates the lowest reflectance of the particular resonant structure 192, and may be as low as approximately 0% of incident light. Peak reflectance frequency 304 indicates a frequency corresponding to maximum reflectance 302 of reflectance profile 300, and may be referred to as the "resonant frequency" of the resonant structure 192 associated with reflectance profile 300. It is noted that in practice, a reflectance profile for some resonant structures 192 may differ significantly from reflectance profile 300 in FIG. 3 in one or more ways. For example, a reflectance profile for one or more resonant structures 192 may be asymmetrical about peak reflectance frequency 304. Alternatively or additionally, a reflectance profile may include multiple local reflectance frequency peaks, rather than a single peak reflectance frequency. Alternatively or additionally, a reflectance profile may be much more irregular than reflectance profile 300.

Output frequency band 351 indicates a band of light frequencies that are emitted from the source 144 that is associated with output spectrum 350. In FIG. 3, output frequency band 351 extends from minimum output frequency 353 to maximum output frequency 352. Thus, the source 144 emits little or no light with a frequency that is less than minimum output frequency 353 or greater than maximum output frequency 352. Peak output frequency 354 indicates a frequency corresponding to the highest intensity light emission by the source 144. It is noted that, in practice, most light sources emit light over a spectrum rather than at a single discrete light frequency, therefore output spectrum 350 may be generally applicable to most or all light sources suitable for use as a source 144.

As shown in FIG. 3, a source 144 that illuminates a particular resonant structure 192 may be selected so that output frequency band 351 of the source 144 overlaps partially or entirely with the reflected frequency band 301 of the particular resonant structure 192. Thus, when the source 144 illuminates the particular resonant structure 192, reflected electromagnetic energy 147 can be measured, for example by sensor array 146 (reflected electromagnetic energy 147 and sensor array 146 are shown in FIGS. 1 and 2). Excluding scattering losses and other secondary effects, reflected electromagnetic energy 147, as measured by sensor array 146, generally has a reflected power 360 equal to the integration in frequency of the multiplication of reflectance profile 300 and output spectrum 350, and is indicated in FIG. 3 as a cross-hatched region.

According to some embodiments, for a particular source 144 illuminating a particular resonant structure 192, reflected power 360 is measured for when the resonant structure 192 is in contact with one or more liquid samples with known refractive index values and/or when the same resonant structure 192 is only in contact with air. The change in value of reflected power 360 at these various conditions may then be used to accurately determine the refractive index value of a liquid sample with an unknown refractive index value, as described below in conjunction with FIGS. 4, 5, and 6.

Figure 4:
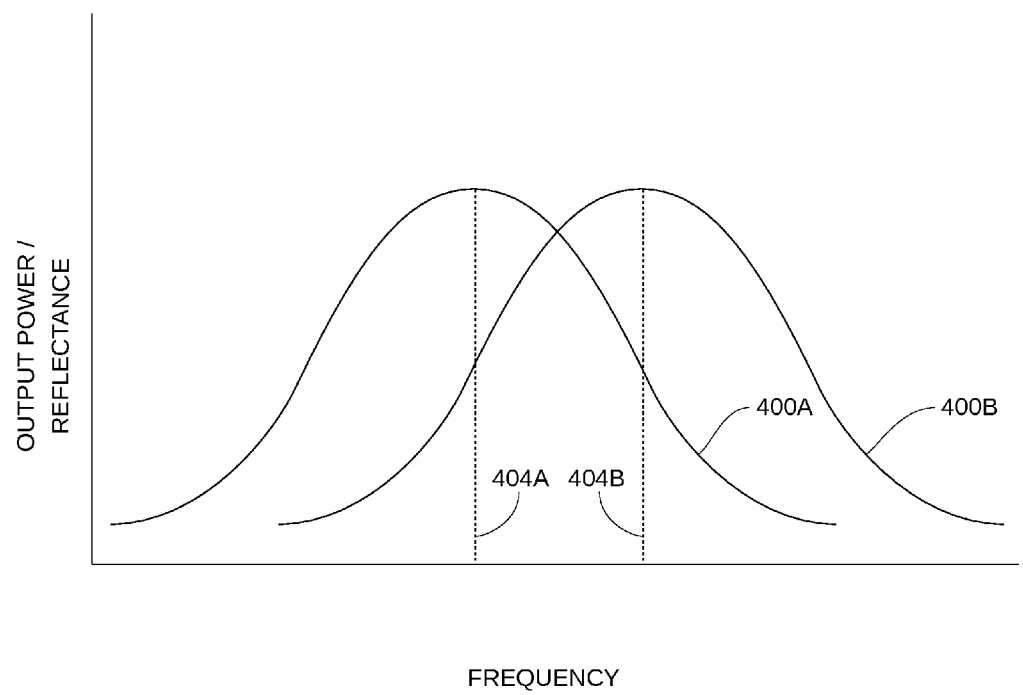
FIG. 4 compares a reflectance profile for an example resonant structure in FIG. 1 and a different reflectance profile for the same example resonant structure, in accordance with at least some embodiments of the present disclosure.

FIG. 4 compares a reflectance profile 400A for an example resonant structure 192 in FIG. 1 and a different reflectance profile 400B for the same example resonant structure 192, in accordance with at least some embodiments of the present disclosure. Reflectance profile 400A illustrates a reflectance (y-axis) of the resonant structure 192 with respect to the frequency of incident light (x-axis) when the resonant structure 192 is in contact with a first material having a first refractive index value, such as a first liquid sample. Reflectance profile 400A includes a peak reflectance frequency 404A indicating a frequency corresponding to maximum reflectance frequency of reflectance profile 400A, and as such is the resonant frequency of the resonant structure 192 when in contact with the first material. Similarly, reflectance profile 400B illustrates a reflectance of the same resonant structure 192 with respect to the frequency of incident light when the resonant structure 192 is in contact with a second material having a second refractive index value, such as a second liquid sample, or in some embodiments, air. Reflectance profile 400B includes a peak reflectance frequency 404B indicating a frequency corresponding to maximum reflectance of reflectance profile 400B, and as such is the resonant frequency of the resonant structure 192 when in contact with the second liquid sample.

Generally, the resonant frequency of a particular resonant structure 192, such as a surface plasmon, a photonic band gap, or the like, is dependent on the medium contacting the resonant structure 192. More specifically, the resonant frequency of the particular resonant structure 192 is strongly dependent on the refractive index value of the medium contacting the particular resonant structure 192. Consequently, the resonant frequency and the entire reflectance profile of a particular resonant structure 192 may change depending on what medium is in contact with the resonant structure 192. Hence, peak reflectance frequency 404A of reflectance profile 400A is a different frequency than peak reflectance frequency 404B of reflectance profile 400B. Furthermore, reflectance profile 400A and reflectance profile 400B generally have different respective values for reflected frequency band, maximum reflectance frequency, and minimum reflectance frequency, even though these two reflectance profiles are both for the same resonant structure 192. The differences between reflectance profile 400A and reflectance profile 400B allow the refractive index value of the liquid sample to be determined, as described below in conjunction with FIG. 5.

Figure 5:
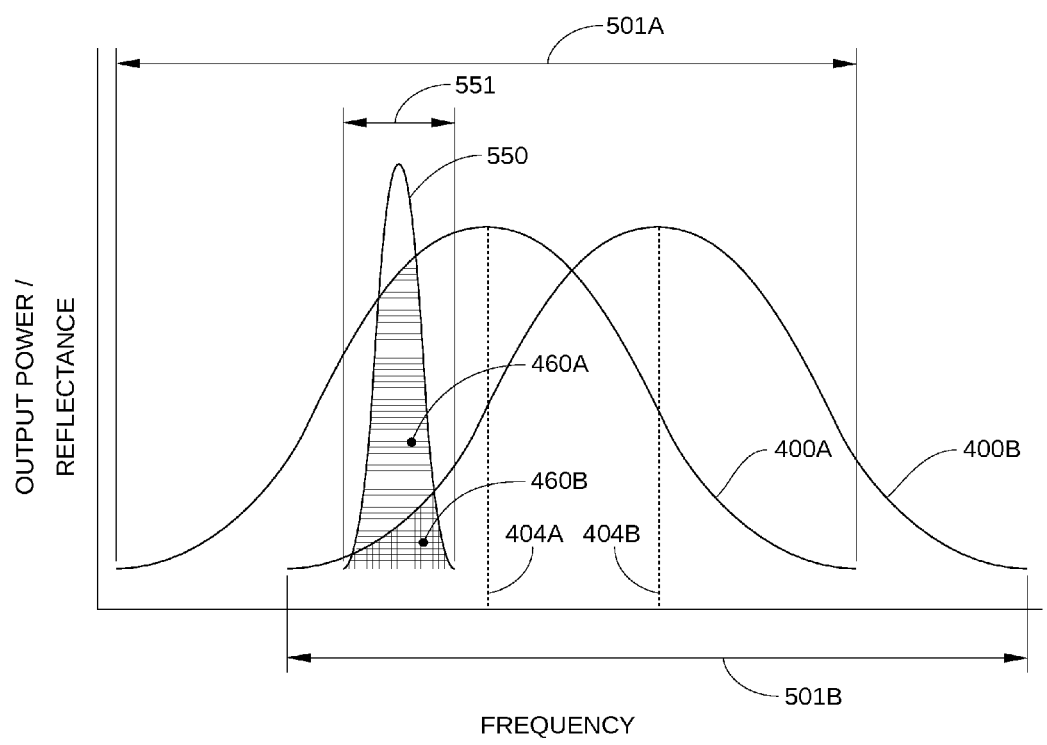
FIG. 5 shows the reflectance profiles of FIG. 4 and an output spectrum for a source, in accordance with at least some embodiments of the present disclosure.

FIG. 5 shows reflectance profile 400A, reflectance profile 400B, and an output spectrum 550 for one of sources 144. As shown, an output frequency band 551 of output spectrum 550 at least partially overlaps a reflected frequency band 501A of reflectance profile 400A and a reflected frequency band 501B of reflectance profile 400B. Consequently, when the source 144 illuminates the resonant structure 192, at least a portion of the incident light is reflected. When the resonant structure 192 is in contact with the first liquid sample, the optical power of the reflected incident light is equal to the integration in frequency of the multiplication of reflectance profile 400A and output spectrum 550, and is indicated by reflected power 460A (horizontally cross-hatched region). When the resonant structure 192 is in contact with the second liquid sample, the optical power of the reflected incident light is equal to the integration in frequency of the multiplication of reflectance profile 400B and output spectrum 550, and is indicated by reflected power 460B (vertically cross-hatched region).

According to some embodiments, a plurality of reference measurements of reflected power may be performed for resonant structure 192 under various conditions, to establish a relationship between measured reflected power and the refractive index of a liquid sample in contact with resonant structure 192. In each such measurement of reflected power, a reference optical power is quantified, such as reflected power 460A and 460B. Each reflected power reference measurement is performed with resonant structure 192 in contact with a different reference liquid, each reference liquid having a known refractive index value. In this way, a relationship between reflected optical power from resonant structure 192 (when illuminated by a particular source 144) and the refractive index value of a liquid sample in contact with resonant structure 192 can be empirically constructed.

Specifically, when resonant structure 192 is in contact with a liquid sample having an unknown refractive index value, such as a liquid containing an unknown concentration of impurities, illuminating resonant structure 192 with the source 144 used in the plurality of reflected power reference measurements described above produces a reflected power similar to reflected power 460A or reflected power 460B. By measuring the reflected power and comparing the measured reflected power to one or more reference reflected powers that correspond to liquid samples having a known refractive index value, the unknown refractive index value of the liquid sample can be determined. Alternatively or additionally, in some embodiments, a curve (or a mathematical expression corresponding to such a curve) may be constructed based on the above-described reference measurements of reflected power. In such embodiments, the curve or mathematical expression may describe the relationship between reflected power measured when source 144 illuminates a resonant structure 192 and the refractive index value of the liquid sample in contact with the resonant structure 192.

In some embodiments, interpolation may be used between the available values of reference reflected powers to more accurately determine the refractive index value of the liquid sample of interest. Alternatively or additionally, in some embodiments, the refractive index value of the liquid sample of interest may be based at least in part on the optical power used by source 144 to generate the measured reflected power. For example, when source 144 illuminates resonant structure 192 with a first optical power for the reflected power reference measurements described above and source 144 illuminates resonant structure 192 with a different optical power when resonant structure 192 contacts a liquid sample of unknown refractive index value, the reflected power measured in the latter case may be scaled to compensate accordingly.

While any technically feasible light source may be suitable for use as one of sources 144, in practice a source having a relatively narrow output frequency band 551 may better facilitate the determination of refractive index value of a liquid in contact with resonant structures 192, as described herein. This is because, as different liquid samples with different refractive index values contact resonant structures 192, larger changes in reflected power may result.

Figure 6:
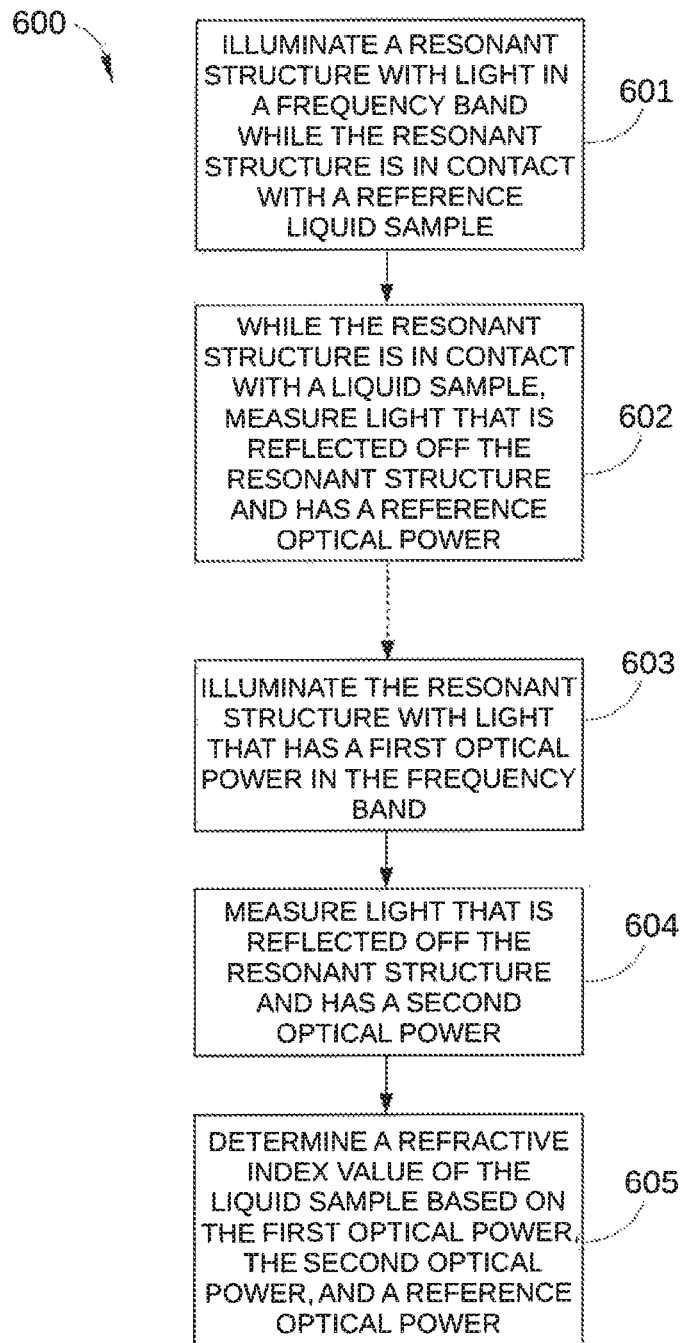
FIG. 6 sets forth a flowchart summarizing an example method to measure refractive index value of a liquid sample, in accordance with at least some embodiments of the present disclosure.

FIG. 6 sets forth a flowchart summarizing an example method 600 to measure refractive index value of a liquid sample, in accordance with at least some embodiments of the present disclosure. Method 600 may include one or more operations, functions or actions as illustrated by one or more of blocks 601, 602, 603, 604, and/or 605. Although the blocks are illustrated in a sequential order, these blocks may also be performed in parallel, and/or in a different order than those described herein. Also, the various blocks may be combined into fewer blocks, divided into additional blocks, and/or eliminated based upon the desired implementation. Additional blocks representing other operations, functions or actions may also be provided. Although method 600 is described in conjunction with refractometer 100 of FIG. 1, any apparatus configured to perform method 600 is within the scope of this disclosure.

Method 600 may begin in block 601 "illuminate a resonant structure with light in a frequency band while the resonant structure is in contact with a reference liquid sample." Block 601 may be followed by block 602 "while the resonant structure is in contact with a liquid sample, measure light that is reflected off the resonant structure and has a reference optical power," block 602 may be followed by block 603 "illuminate the resonant structure with light that has a first optical power in the frequency band," block 603 may be followed by block 604 "measure light that is reflected off the resonant structure and has a second optical power," and block 604 may be followed by block 605 "determine a refractive index value of the liquid sample based on the first optical power, the second optical power, and a reference optical power."

In block 601, refractometer 100 illuminates a resonant structure, such as one of resonant structures 192, with light in a particular frequency band while resonant structure 192 is in contact with a reference liquid sample. The frequency band may be in the (human) visible portion, the near infrared portion, and/or or the near ultraviolet portion of the electromagnetic spectrum. Generally, the resonant structure is formed on an optical surface, such as surface 191. In addition, in block 601 the reference liquid sample has a known refractive index value.

In block 602, refractometer 100 measures light that is reflected off resonant structure 192 with a reference optical power, for example using sensor array 146. In at least some embodiments, the reference optical power so measured either includes or is limited to the particular frequency band of the light used to illuminate resonant structure 192 in block 601. In subsequent operation, refractometer 100 can determine a refractive index value for a liquid sample by measuring a reflected power from resonant structure 192 and comparing the measured reflected power to one or more reference reflected powers. For example, the one or more reference optical powers may be measured as described in blocks 601 and 602.

In some embodiments, refractometer 100 may repeat blocks 601 and 602 multiple times, each time with a different reference liquid sample in contact with resonant structure 192. Since each of the different reference liquid samples used may have a different but known refractive index value, a relationship may be quantified between measured reflected power and the refractive index value of a reference liquid sample in contact with resonant structure 192. In this way, an unknown refractive index value of a liquid sample may be determined by measuring reflected power from resonant structure 192.

Additionally or alternatively, refractometer 100 may perform blocks 601 and 602 using light in different frequency bands, thereby measuring reference optical powers for multiple frequency bands. Additionally or alternatively, in such embodiments refractometer may illuminate a different resonant structure when light of a different frequency band is used. Furthermore, in some embodiments, light in multiple frequency bands may be used to illuminate a single resonant structure 192. For example, two or more sources 144 in FIG. 1, each emitting light in a different frequency band, may be used to illuminate the same resonant structure 192. Once such embodiment is illustrated in FIG. 7.

Figure 7:
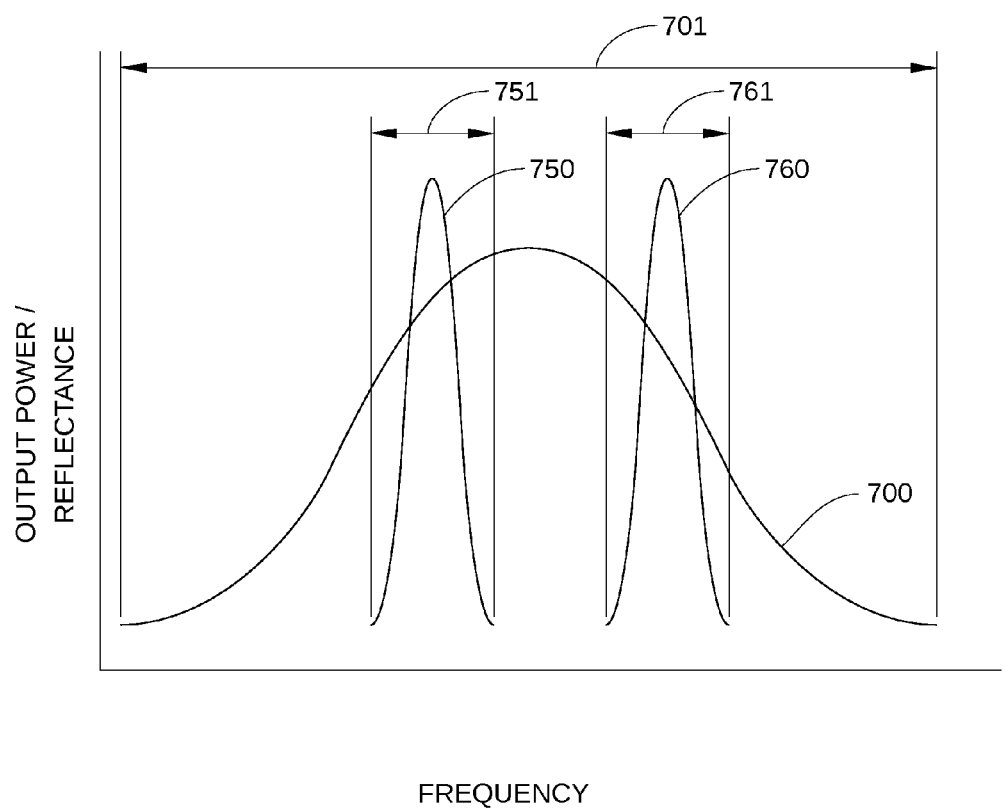
FIG. 7 shows a reflectance profile for a particular resonant structure, a first output spectrum for a first source and a second output spectrum for a second source, in accordance with at least some embodiments of the present disclosure.

FIG. 7 shows a reflectance profile 700 for a particular resonant structure 192, a first output spectrum 750 for a first source and a second output spectrum 760 for a second source, in accordance with at least some embodiments of the present disclosure. As shown, an output frequency band 751 of first output spectrum 750 at least partially overlaps a reflected frequency band 701 of reflectance profile 700 and an output frequency band 761 of second output spectrum 760 at least partially overlaps reflected frequency band 701. Consequently, in such embodiments (e.g., embodiments in which refractometer 100 performs blocks 601 and 602 using light in different frequency bands), refractometer 100 can subsequently determine the refractive index value of a sample liquid in contact with resonant structures 192 for multiple frequency bands. These multiple frequency bands may span a much wider frequency spectrum than conventional refractometers, which are generally designed for measuring a refractive index value of a material in a specific frequency or narrow frequency band. Additionally or alternatively, blocks 601 and 602 may be performed by a different refractometer than refractometer 100, and the results of blocks 601 and 602 may be stored in refractometer 100 for use during normal operation of refractometer 100.

Returning to FIG. 6, in block 603, while resonant structure 192 is in contact with a liquid sample that has a refractive index value that is unknown, refractometer 100 illuminates resonant structure 192 with light that has a first optical power in the frequency band that was used to illuminate the same resonant structure 192 in block 601. For example, the same source 144 use illuminate the resonant structure 192 in block 601 may also be used in block 603. In some embodiments, refractometer 100 illuminates resonant structure 192 with substantially the same optical power in the frequency band as the optical power used to illuminate resonant structure 192 in block 601. In other embodiments, a different optical power in the frequency band may be used in block 603 than was used in block 601, in which case the determination of the refractive index of the liquid sample in block 605 is scaled accordingly.

In block 604, refractometer 100 measures light that is reflected off resonant structure 192 (e.g., electromagnetic energy 147 in FIG. 1), where the reflected light has a second optical power. Generally, sensor array 146 or any other suitable sensor for measuring the light reflected off resonant structure 192 may be employed in block 604.

In block 605, refractometer 100 determines a refractive index value of the liquid sample based on the first optical power, the second optical power, and one or more reference optical powers. For example, refractometer 100 may compare the second optical power of a particular resonant structure 192 to one or more reference optical powers associated with that particular resonant structure 192, and calculate a refractive index value of the liquid sample accordingly. Interpolation between the reference optical powers may be used and, when the first optical power differs significantly from the optical power used to generate one or more of the reference optical powers, scaling of the second optical power may be employed before such a calculation is performed.

It is noted that the refractive index value determined by refractometer 100 in block 605 is for a particular wavelength band. In some embodiments, blocks 603-605 may be repeated using light in different frequency bands to illuminate one or more of resonant structures 192. In this way, a refractive index value for a liquid sample can be determined for multiple frequency bands. These frequency bands may span a relatively large range of frequencies, for example from the near infrared portion of the electromagnetic spectrum to the near ultraviolet portion of the electromagnetic spectrum.

Figure 8:
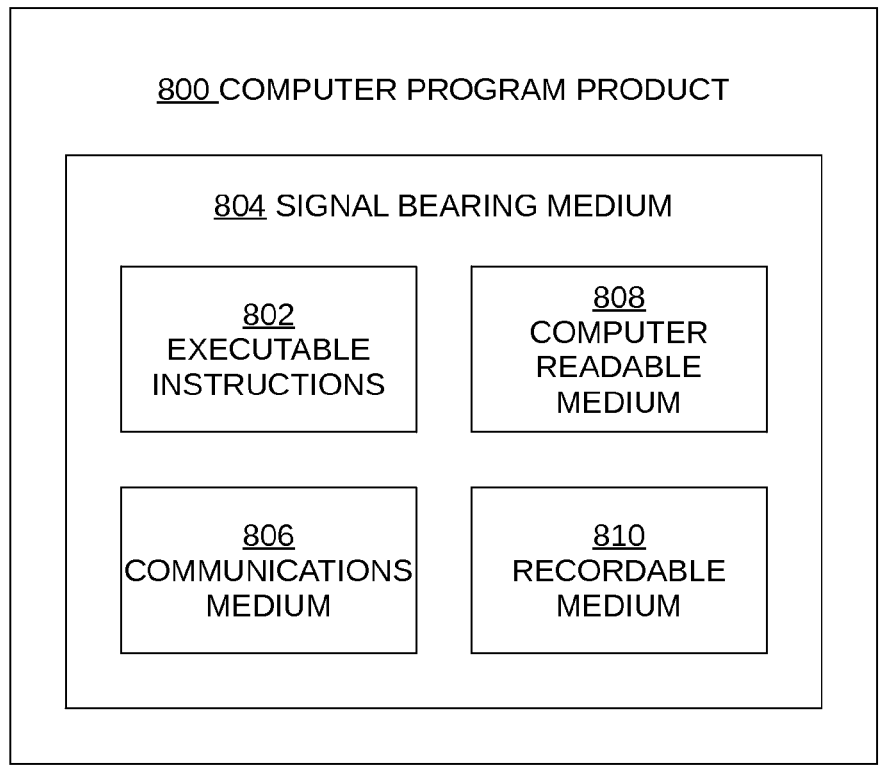
FIG. 8 is a block diagram of a computer program product to implement a method to analyze skin with electromagnetic energy.

FIG. 8 is a block diagram of a computer program product 800 to implement a method to analyze skin with electromagnetic energy, in accordance with at least some embodiments of the present disclosure. Computer program product 800 may include a signal bearing medium 804. Signal bearing medium 804 may include one or more sets of executable instructions 802 that, when executed by, for example, a processor of a computing device, may provide at least the functionality described above with respect to FIGS. 1-7.

In some implementations, signal bearing medium 804 may encompass a non-transitory computer readable medium 808, such as, but not limited to, a hard disk drive, a Compact Disc (CD), a Digital Video Disk (DVD), a digital tape, memory, etc. In some implementations, signal bearing medium 804 may encompass a recordable medium 810, such as, but not limited to, memory, read/write (R/W) CDs, R/W DVDs, etc. In some implementations, signal bearing medium 804 may encompass a communications medium 806, such as, but not limited to, a digital and/or an analog communication medium (e.g., a fiber optic cable, a waveguide, a wired communications link, a wireless communication link, etc.). Computer program product 800 may be recorded or otherwise stored on non-transitory computer readable medium 808 or another similar recordable medium 810.

Figure 9:
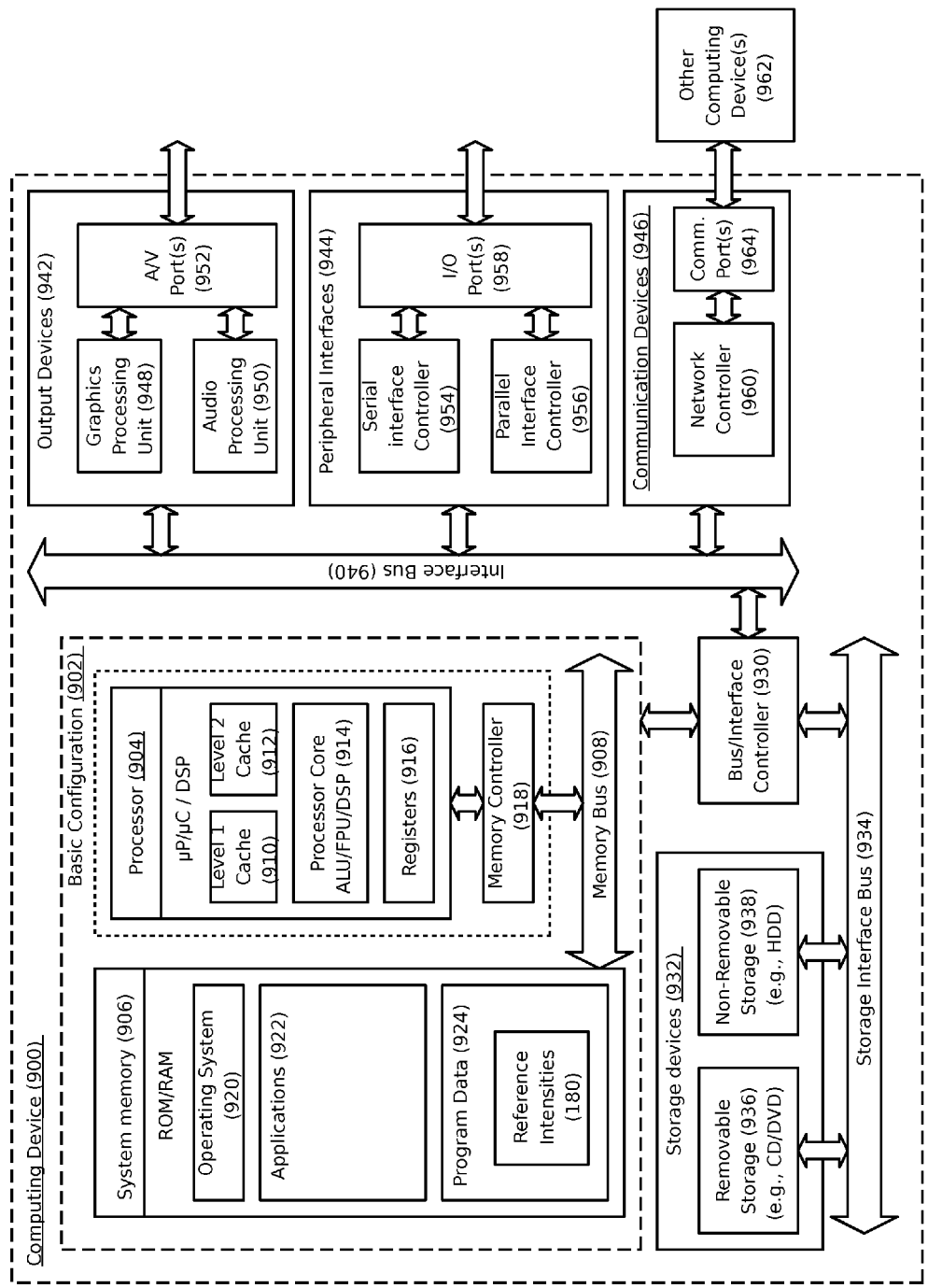
FIG. 9 is a block diagram illustrating an example computing device, all arranged in accordance with at least some embodiments of the present disclosure.

FIG. 9 is a block diagram illustrating an example computing device 900 that may implement at least some embodiments of the present disclosure. In a very basic configuration 902, computing device 900 typically includes one or more processors 904 and a system memory 906. A memory bus 908 may be used for communicating between processor 904 and system memory 906.

Depending on the desired configuration, processor 904 may be of any type including but not limited to a microprocessor (µP), a microcontroller (µC), a digital signal processor (DSP), or any combination thereof. Processor 904 may include one more levels of caching, such as a level one cache 910 and a level two cache 912, a processor core 914, and registers 916. An example processor core 914 may include an arithmetic logic unit (ALU), a floating point unit (FPU), a digital signal processing core (DSP Core), or any combination thereof. An example memory controller 918 may also be used with processor 904, or in some implementations memory controller 918 may be an internal part of processor 904.

Depending on the desired configuration, system memory 906 may be of any type including but not limited to volatile memory (such as RAM), non-volatile memory (such as ROM, flash memory, etc.) or any combination thereof. System memory 906 may include an operating system 920, one or more applications 922, and program data 924. Application 922 may provide at least the functionality described above with respect to FIGS. 1-7. Program data 924 may be useful for operation with application 922 and include, for example, one or more reference intensities 180, as are described herein. In some embodiments, application 922 may be arranged to operate with program data 924 on operating system 920. This described basic configuration 902 is illustrated in FIG. 9 by those components within the inner dashed line.

Computing device 900 may have additional features or functionality, and additional interfaces to facilitate communications between basic configuration 902 and any required devices and interfaces. For example, a bus/interface controller 930 may be used to facilitate communications between basic configuration 902 and one or more data storage devices 932 via a storage interface bus 934. Data storage devices 932 may be removable storage devices 936, non-removable storage devices 938, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 906, removable storage devices 936 and non-removable storage devices 938 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 900. Any such computer storage media may be part of computing device 900.

Computing device 900 may also include an interface bus 940 for facilitating communication from various interface devices (e.g., output devices 942, peripheral interfaces 944, and communication devices 946) to basic configuration 902 via bus/interface controller 930. Example output devices 942 include a graphics processing unit 948 and an audio processing unit 950, which may be configured to communicate to various external devices such as a display or speakers via one or more A/V ports 952. Example peripheral interfaces 944 include a serial interface controller 954 or a parallel interface controller 956, which may be configured to communicate with external devices such as input devices (e.g., keyboard, mouse, pen, voice input device, touch input device, etc.) or other peripheral devices (e.g., printer, scanner, etc.) via one or more I/O ports 958. An example communication device 946 includes a network controller 960, which may be arranged to facilitate communications with one or more other computing devices 962 over a network communication link, such as, without limitation, optical fiber, Long Term Evolution (LTE), 3G, WiMax, via one or more communication ports 964.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 900 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 900 may also be implemented as a personal computer including both laptop computer and non-laptop computer configurations or as a server device.

In some examples, a method to measure refractive index of a liquid sample comprises contacting the liquid sample with an optical surface that includes a resonant structure, illuminating the resonant structure with light that has a first optical power in a frequency band, and measuring light that is reflected off the resonant structure and has a second optical power in the frequency band. A refractive index value of the liquid sample may be determined based on the first optical power, the second optical power, and in some examples, a reference optical power may be used in the determination of the refractive index. A reference optical power may include, for example, an optical power reflected from the resonant structure, or a similar reference structure, in contact with a liquid sample of known refractive index, or in contact with air or other medium, or in any other predetermined configuration. In some examples, determination of a reference power may include measurement of the light emission of the electromagnetic emitter, or other potentially equivalent parameter, such as the drive current of an LED.

In some examples, a resonant structure may comprise a photonic crystal. A photonic crystal may comprise, for example, an arrangement of particles, such as a periodic arrangement of particles (such as microspheres and the like). In some examples, a photonic crystal may comprise an arrangement of voids (such as apertures and the like) in a matrix medium. In some examples, a resonant structure may comprise channels to allow a liquid sample to more rapidly permeate the resonant structure. In some examples, a resonant structure may comprise a membrane, such as a dielectric and/or metal membrane, having an array of apertures disposed therein. In some examples, a resonant structure may comprise an arrangement of microspheres on a surface, for example metal and/or dielectric microspheres. In some examples, a resonant structure may comprise a thin metal film, for example having a thickness in the range 1-100 microns, or may comprise a multilayer optical structure. In some examples, a resonant structure may be configured so that its optical properties vary appreciably with variation in a refractive index of a liquid sample. In some examples, the liquid sample may be adjacent the resonant structure (for example, as a liquid film adjacent a metal film), and in some examples the liquid sample may be within or part of a resonant structure (for example, filling voids within a photonic crystal). In some examples, a photonic crystal may have a feature dimension (such as a particle diameter, aperture diameter, particle spacing, hole spacing, or other parameter) approximately equal to (e.g. within an order of magnitude of) a wavelength in the frequency band.

In some examples, an apparatus configured to measure a refractive index value of a liquid sample comprises an optical surface that includes a resonant structure configured to be brought into contact with the liquid sample, a first electromagnetic emitter configured to illuminate the resonant structure using light that has a first optical power in a first wavelength band, a sensor configured to receive light reflected from the resonant structure that has a second optical power in the frequency band; and a microprocessor that is communicably coupled to the electromagnetic emitter and the sensor and is configured to determine a refractive index value of the liquid sample in the frequency band based on the first optical power, the second optical power, and, optionally, a reference optical power. In some example, the first electromagnetic emitter may comprise a light emitting diode (LED). In some examples, the first wavelength band may include or correspond to the emission spectrum of a LED. In some examples, the resonant structure may be configured to have a reflectivity that varies appreciably with refractive index of the liquid sample within the first wavelength band, or a wavelength therein. For example, the resonant structure may have one or more reflectivity and/or absorption bands, having optical characteristics that vary appreciably with the refractive index of the liquid sample.

In some examples, the temperature of the liquid sample may be determined, for example by a temperature sensor, allowing the refractive index to be determined for a known temperature. In some examples, an apparatus may comprise a plurality of electromagnetic emitters, such as a plurality of LEDs, for example LEDs having different emission wavelengths. For example, an apparatus may comprise one or more of a near-IR, red, orange, yellow, green, blue, violet, and/or UV LED, or other wavelength emission LED or other light source. In some examples, one or more of the plurality of electromagnetic emitters may be selected for refractive index determination, for example based on one or more parameters such as, for example: absorption, fluorescence or other optical property of the liquid sample; refractive index of the liquid sample; properties of the resonant structure; temperature, cloudiness, contamination or other characteristics of a liquid sample; and the like. A resonant structure may be removable from the apparatus, for example for cleaning or replacement.

In sum, embodiments of the present disclosure provide systems and methods to measure refractive index of a liquid without bulky precision optics. By empirically determining a relationship between the refractive index of a liquid sample and a measured reflected power from a resonant structure when in contact with the liquid sample, the refractive index of a liquid can be determined by measuring this reflected power. Furthermore, using multiple light sources of different frequencies, the refractive index of the liquid sample can be determined over a very broad spectral range, for example from ultra-violet to far infrared. In this way, a compact, low cost apparatus can accurately determine the refractive index of liquid samples over a very broad spectral range and without changing optical elements for different frequencies of light.

There is little distinction left between hardware and software implementations of embodiments of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

I claim:

1. A method to measure refractive index of a liquid sample that is in contact with an optical surface that includes a resonant structure, the method comprising:
   while the resonant structure is in contact with the liquid sample, illuminating the resonant structure with light that has a first optical power in a frequency band;
   measuring light that is reflected off the resonant structure and has a second optical power in the frequency band; and
   determining a refractive index value of the liquid sample based on the first optical power, the second optical power, and a reference optical power.

2. The method of claim 1, further comprising:
   prior to the resonant structure being in contact with the liquid sample, illuminating the resonant structure with light that has a third optical power in the frequency band while the resonant structure is in contact with a reference liquid sample with a known refractive index value; and
   measuring light that is reflected off the resonant structure with the reference optical power.

3. The method of claim 1, wherein the light used to illuminate the resonant structure includes light in one of the ultra-violet wavelength band or in the infra-red wavelength band.

4. The method of claim 1, wherein the resonant structure is configured so that the second optical power varies as a function of the refractive index value of the liquid sample.

5. The method of claim 4, wherein the resonant structure comprises a photonic crystal with a photonic band gap that overlaps at least a portion of the frequency band.

6. The method of claim 4, wherein the resonant structure comprises a structure configured to generate a surface plasmon that at least partially reflects light with a frequency in the frequency band.

7. The method of claim 6, wherein illuminating the resonant structure comprises directing polarized light onto the resonant structure.

8. The method of claim 1, further comprising illuminating an additional resonant structure with light that has a third optical power in a second frequency band.

9. The method of claim 8, further comprising:
   measuring light that is reflected off the additional resonant structure and has a fourth optical power in the second frequency band;
   determining a refractive index value of the liquid sample in the second frequency band based on the third optical power, the fourth optical power, and an additional reference optical power.

10. The method of claim 1, wherein determining the refractive index value of the liquid sample comprises:
    comparing the second intensity to the reference intensity; and
    selecting for the refractive index value of the liquid sample a refractive index value associated with the reference intensity.

11. The method of claim 10, wherein selecting the refractive index value associated with the reference intensity comprises determining the refractive index value associated with the reference intensity based on the reference intensity and an empirically determined relationship between a refractive index in the frequency band of a test liquid in contact with the resonant structure and a reflectance of the resonant structure when in contact with the test liquid.

12. An apparatus to measure refractive index value of a liquid sample, the apparatus comprising:
    an optical surface that includes a resonant structure configured to be brought into contact with the liquid sample;
    a first electromagnetic emitter configured to illuminate the resonant structure using light that has a first optical power in a first wavelength band;
    a sensor configured to receive light reflected from the resonant structure that has a second optical power in the frequency band; and
    a microprocessor that is communicably coupled to the electromagnetic emitter and the sensor and is configured to
    determine the refractive index value of the liquid sample in the frequency band based on the first optical power, the second optical power, and a reference optical power.

13. The apparatus of claim 12, further comprising a second electromagnetic emitter configured to illuminate a second resonant structure with light in a second wavelength band.

14. The apparatus of claim 13, wherein the first wavelength band includes a visible wavelength band and the second wavelength band includes one of an infra-red wavelength band or an ultra-violet wavelength band.

15. The apparatus of claim 12, wherein the optical surface is configured to be submerged in the liquid sample.

16. The apparatus of claim 12, wherein the optical surface is configured to have the liquid sample placed thereon.

17. The apparatus of claim 12, wherein the resonant structure is configured so that the second optical power varies as a function of the refractive index value of the liquid sample.

18. The apparatus of claim 17, wherein the resonant structure comprises one of a photonic crystal with a photonic band gap that overlaps at least a portion of the frequency band and a structure configured to generate a surface plasmon that at least partially reflects light with a frequency in the frequency band.

19. The apparatus of claim 12, wherein the microprocessor is further configured to determine the refractive index value of the liquid sample by:
    comparing the second intensity to the reference intensity; and
    selecting for the refractive index value of the liquid sample a refractive index value associated with the reference intensity.

* * * * *